United States Patent [19]

Wang

[11] Patent Number: 4,847,388

[45] Date of Patent: Jul. 11, 1989

[54] POLYCYCLIC UNSATURATED ETHERS AND ESTERS

[75] Inventor: Pen C. Wang, Houston, Tex.

[73] Assignee: Shell Oil Company, Houston, Tex.

[21] Appl. No.: 245,433

[22] Filed: Sep. 16, 1988

[51] Int. Cl.$^4$ ............................................. C07D 491/00
[52] U.S. Cl. ..................... 548/410; 540/543;
544/6; 544/70; 544/230; 546/15; 548/147;
548/216; 548/323
[58] Field of Search ............... 548/410, 147, 216, 323;
540/543; 544/6, 70, 230; 546/15

[56] References Cited

U.S. PATENT DOCUMENTS 4,100,140  7/1978  Zahir ................................ 526/219.6
4,468,524  8/1984  Zahir ................................ 560/138

Primary Examiner—C. Warren Ivy
Assistant Examiner—Alex H. Walker

[57] ABSTRACT

A novel class of unsaturated polycyclic ethers and esters comprises unsaturated ether and ester derivatives of a hydroxyaryl-substituted [4.4] spirodilactams having nitrogen atoms in the 1- and 6-positions of the spiro ring system and having the hydroxyaryl groups attached to each spiro ring nitrogen. Such unsaturated ethers and esters react with conventional curing agents to produce cured, insoluble products having high glass transition temperatures.

24 Claims, No Drawings

POLYCYCLIC UNSATURATED ETHERS AND ESTERS

FIELD OF THE INVENTION

This invention relates to a novel class of unsaturated ether or ester derivatives of spirodilactams having hydroxyaryl substituents. More particularly, the invention relates to unsaturated ether or ester derivatives of a hydroxyaryl-substituted 1,6-diazaspiro[4.4]nonane-2,7-dione, to the process of producing such derivatives and to cured products derived therefrom.

BACKGROUND OF THE INVENTION

Unsaturated ether or ester derivatives of polyhydric phenols are well known as a class of compounds that can be cured or crosslinked to produce insoluble products which exhibit good solvent resistance and mechanical properties as well as high heat distortion temperature. Such unsaturated ethers or esters are crosslinked by reaction with catalytic or polyfunctional curing agents to produce tough, heat resistant products which are processed by conventional methods into sheets, laminates with fiber glass or other reinforcements or shaped articles and the crosslinked products are also useful in adhesive formulations.

As indicated, much of the technology is broadly conventional. The disclosure of Zahir et al, U.S. Pat. No. 4,100,140 is illustrative. The compound 2,2-di(4-hydroxyphenyl)propane, also known as bisphenol A or BPA, is converted to the sodium salt and reacted with allyl chloride to produce the allyl ether derivative of BPA, i.e., 2,2-di(4-allyloxyphenyl)propane. This diallyl ether is rearranged to the diallyl-substituted BPA which is cured, but the diallyl ether is also curable without rearrangement. Curing takes place, for example, by reacting the diallyl ether with an imide-containing curing agent.

Other types of unsaturated derivatives of polyhydric phenols which are cured by such conventional techniques include the acrylate and methacrylate esters of polyhydric phenols described by Zahir et al in U.S. Pat. No. 4,468,524.

On some occasions, the cured products which provide the more desirable properties, particularly in high temperature applications, are produced from unsaturated derivatives of aromatic phenolic compounds having polycyclic structures wherein some or all the rings share common atoms with other rings of the polycyclic structure. It would be of advantage to provide a novel class of unsaturated derivatives of phenolic compounds having a plurality of rings within the molecular structure. Such unsaturated derivatives react with conventional curing agents to produce insoluble cured products of good properties.

SUMMARY OF THE INVENTION

The present invention relates to a novel class of unsaturated derivatives of hydroxyaryl-substituted [4.4]spirodilactam compounds and to cured or crosslinked products derived therefrom by reaction with a curing agent. More particularly, the invention relates to unsaturated ether and ester derivatives of a 1,6-diazaspiro[4.4]nonane-2,7-dione compound having hydroxyaryl-containing substituents on the ring nitrogen atoms of the spirodilactam ring system.

DESCRIPTION OF THE INVENTION

The novel spirodilactam derivatives of the invention are novel unsaturated ether or ester derivatives of 1,6-diazaspiro[4.4]nonane-2,7-dione which is substituted on each ring nitrogen with a hydroxy-containing substituent and is optioally substituted in the 3-,4-, 8- and 9-positions with cyclic or acyclic substituents. One class of such spirodilactams is represented by the formula

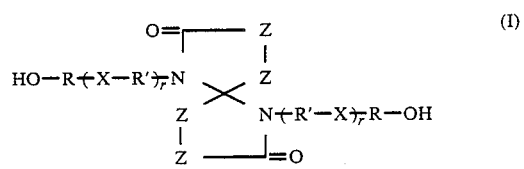

wherein Z independently is

in which Z' independently is hydrogen, lower alkyl of up to 4 carbon atoms inclusive, preferably methyl or halogen, preferably the lower halogen fluoro and chloro, or Z is such that two adjacent Z groups taken together form a ring system Z" of from 5 to 7 ring atoms, up to two of which are heteroatoms selected from nitrogen atoms, oxygen atoms or sulfur atoms with the remainder of the ring atoms being carbon atoms, there being up to 15 carbon atoms in each Z", two of which form a bridge which connects a carboxy or a carbonyl carbon, i.e., one of the carbon atoms in the 2- or 7-position, with the spiro carbon atom, i.e., the carbon atom common to the two indicated rings. In the above formula I, R independently is aromatic of up to 15 carbon atoms and up to 2 aromatic rings, inclusive, R' is R or an aliphatic group of up to 10 carbon atoms inclusive. Each of R and R' are hydrocarbyl, i.e., contain only atoms of carbon and hydrogen, or are substituted-hydrocarbyl containing additional atoms in the form of inert substituents such as halogen, preferably middle halogen chlorine or bromine. The term r in the above formula I is 0 or 1 and X is a direct valence bond, alkylene of up to 8 carbon atoms inclusive, oxo, thio, sulfonyl, carbonyl, dioxyphenylene, i.e.,

2,2-di(oxyphenyl)propane, i.e.,

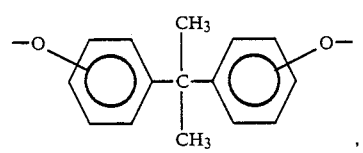

or dioxydiphenylene, i.e.,

Spirodilactams of a considerable variety of structures are therefore suitably employed as a precursor of the unsaturated ether or ester derivatives of the invention. In the embodiment wherein the Z moieties of the above formula I are acyclic, the spirodilactam is illustrated by 1,6-di(4-hydroxyphenyl)-1,6-diazaspiro[4.4]nonane-2,7-dione, 1,6-di(3-hydroxy-4-chlorophenyl)-3,8-dimethyl-1,6-diazaspiro[4.4]nonane-2,7-dione, 1,6-di[4-(3-hydroxybenzoyl)phenyl]-1,6-diazaspiro[4.4]nonane-2,7-dione, 1,6-di(4-hydroxyphenyl)-3,3,4,4,8,8,9,9-octamethyl-1,6-diazaspiro[4.4]nonane-2,7-dione, 1,6-di[4-(4'-hydroxybiphenyl)-3,3-dimethyl-1,6-diazaspiro[4.4]nonane-2,7-dione, 1,6-di[2-(4-(4-hydroxyphenyl)propyl]-1,6-diazaspiro[4.4]nonane-2,7-dione and 1,6-di[4-(4-hydroxyphenylisopropyl)-phenyl]-1,6-diazaspiro[4.4]nonane-2,7-dione. In the embodiment wherein adjacent Z moieties on each ring form a cyclic structure fused to the spiro ring system, illustrative spirodilactams include 1,6-di(4-hydroxyphenyl)-3,4-8,9-dibenzo-1,6-diazaspiro[4.4]nonane-2,7-dione, 1,6-di[4-(4-hydroxyphenyl)-phenyl]-3,4-8,9-dipyrido-1,6-diazaspiro[4.4]nonane-2,7-dione and 1,6-di[4-(4-hydroxyphenyloxy)phenyl]-3,4-8,9-di(cyclopentano)-1,6-diazaspiro[4.4]nonane-2,7-dione. Also suitable are those spiro-dilactams wherein one spiro ring has a fused ring substituent and the other spiro ring is free of fused ring substituents, e.g., 1,6-di(4-hydroxyphenyl)-3,4-benzo-8-methyl-1,6-diazaspiro[4.4]nonane-2,7-dione and 1,6-di[1-(4-hydroxynaphthyl)-3,4-(cyclohexano)-1,6-diazaspiro[4.4]-nonane-2,7-dione.

In general, the compounds of the above formula I wherein R and R' are aromatic and hydrocarbon are preferred, especially such compounds wherein each r is 0. The class of 1,6-di(hydroxyphenyl) spirodilactams is particularly preferred. Within the spirodilactam portion of the molecule, spirodilactam rings substituted with hydrogen, methyl or fused with benzo rings are generally preferred, particularly the 1,6-diazaspiro[4.4]-nonane-2,7-dione.

The hydroxyaryl-substituted spirodilactams of the above formula I are compounds which are described and claimed as compositions of matter in copending U.S. patent application Ser. No. 245,618, filed Sept. 16, 1988 (Docket No. T-4258 G). The general method of production, also described in this copending application and copending U.S. patent application Ser. No. 172,000 filed Mar. 23, 1988 and Ser. No. 172,052 filed Mar. 23, 1988, incorporated herein by reference, is by reaction of at least one hydroxy-containing primary amino compound and a spirodilactam precursor. In terms of the spirodilactam of the above formula I, the hydroxy-containing primary amino compound is represented by the formula

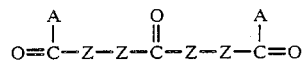

wherein R, R', r and X have the previously stated meanings. The spirodilactam precursor is a 4-oxoheptanedioic acid compound or a 1,6-dioxaspiro[4.4]nonane-2,7-dione. In terms of the spirodilactam of the above formula I, the 4-oxoheptanedioic acid compound spirolactam precursors are represented by the formula

wherein Z has the previously stated meaning and A is hydroxy, lower alkoxy of up to 4 carbon atoms inclusive or halo, preferably chloro or bromo. The spirodilactone spirolactam precursor, in terms of the spirodilactams of formula I, is represented by the formula $$\begin{matrix} O= & & Z \\ & & \\ O & & Z \\ & \times & \\ Z & & O \\ & & \\ Z & & =O \end{matrix}$$ (III)

wherein Z has the previously stated meaning.

Many of the acyclic 4-oxoheptanedioic acid compounds are known, but the esters are also produced by the reaction of formaldehyde and unsaturated carboxylic acid esters by the process disclosed and claimed in copending U.S. patent application Ser. No. 171,999, filed Mar. 23, 1988 (Docket No. T-4143), now U.S. Pat. No. 4,800,231. Interconversion of the acids, esters or acid halides of formula II is by conventional methods. The production of 4-oxoheptanedioic acid compounds of formula II which contain cyclic moieties is by the process of Cava et al, J. Am. Chem. Soc., 20, 6022 (1955). The spirodilactones of formula III are produced by the process of Pariza et al, Synthetic Communications, Vol. 13 (3), pp. 243–(1983). Production of the spirodilactones having additional rings fused to the spiro ring structure is by the process of U.S. Pat. No. 1,999,181.

The hydrogen-containing primary amino compound and the spirolactam precursor react in a molar ratio of 2:1 although in practice reactant ratios from about 8:1 to about 1:1.5 are satisfactory. Reactant ratios of hydroxy-containing primary amino compound to spirolactam precursor which are substantially stoichiometric are preferred. Reaction is conducted in a liquid phase solution in an inert reaction diluent such as a N,N-dialkylamide, e.g., N,N-dimethylacetamide or N,N-dimethylformamide. Reaction takes place under reaction conditions at an elevated temperature, typically from about 80° C. to about 250° C., and at a reaction pressure sufficient to maintain the reaction mixture in a liquid phase, e.g., pressures up to about 20 atmospheres, Subsequent to reaction the spirolactam product is recovered from the product mixture by conventional methods such as solvent removal, precipitation and chromatographic separation. Recovery of the spirolactam is not required, however, and particularly in cases where substantially stoichiometric quantities of reactants were employed the spirodilactam may be reacted further in situ to form derivatives such as the unsaturated ether or ester derivatives of the invention.

The unsaturated derivatives of the hydroxyaryl-substituted spirodilactams are ether or ester derivatives of the hydroxyaryl substituents derivatized at the hydroxyl group through ether or ester formation. The unsaturated moiety which becomes bound to the oxygen of the oxyaryl moiety (derived from the hydroxyaryl moiety) is a group of up to 10 carbon atoms inclusive which contains carbon-carbon unsaturation located at least adjacent to the carbon atom of the unsaturated moiety which is bound to a oxyaryl residue of the hydroxyaryl-substituted spirodilactam. Although unsaturated moieties of a number of types are useful in the ether or ester derivatives of the invention, the preferred unsaturated ether or unsaturated ester moieties are selected from 2-alkenyl, 2-alkynyl, vinylarylmethyl and 2-alkenoyl. Illustrative alkenyl groups include allyl, methallyl and crotyl, which alkynyl groups include propargyl and 2-octynyl. Vinylarylmethyl groups are exemplified by 4-styrylmethyl and 5-vinyl-1-naphthyl. The alkenoyl groups present when ester derivatives are desired include acrylyl, methacryl, 2,4-hexadienoyl and 2-hexenoyl. Preferred unsaturated moieties are allyl, propargyl and 4-vinylstyrylemthyl in the case of ether derivatives and acrylyl and methacrylyl when ester derivatives are contemplated.

These preferred derivatives of the hydroxyaryl-substituted spirodilactams are represented by the formula

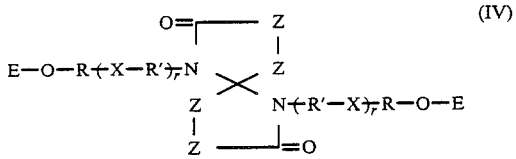

(IV)

wherein R, R', X, r and Z have the previously stated meaning and E independently is an unsaturated moiety of up to 10 carbon atoms inclusive containing carbon-carbon unsaturation at least adjacent to the carbon atoms of E through which E is bound to the oxyaryl moiety. E is preferably allyl, propargyl, 4-styrylmethyl, acrylyl or methacrylyl.

These derivatives are typically produced by reacting a compound containing the desired unsaturated moiety with an alkali metal salt of the hydroxyaryl-substituted spirodilactam. Although lithium, sodium, potassium, rubidium or cesium salts of the hydroxyaryl-substituted spirodilactams are usefully employed in the production of the unsaturated derivatives of the invention, the use of a sodium salt or a potassium salt is preferred. In one modification the alkali metal salt of the hydroxyaryl-substituted spirodilactam is produced by contacting the spirodilactam with a stoichiometric quantity of an alkali metal hydroxide, i.e., substantially 2 moles of alkali metal hydroxide per mole of spirodilactam. Sodium hydroxide or potassium hydroxide is preferred. Reaction is conducted in the liquid phase in a suitable reaction solvent such as N,N-dimethylacetamide or N,N-dimethylformamide while removing the water present or formed by distillation, preferably azeotropic distillation employing a second solvent such as toluene or ethylbenzene with which water forms an azeotrope. The alkali metal salt of the hydroxyaryl substituted spirodilactam is isolated if desired by conventional methods such as solvent removal but the salt is typically used in situ in the media of its production for the reaction with the compound containing the unsaturated moiety.

The unsaturated moiety, E, is provided to the reaction with the alkali metal salt of the hydroxyaryl-substituted spirodilactam in the form of the halide or alkoxide. The compound employed as the reactant which contains the unsaturated moiety is therefore of the formula

E-G (V)

wherein E has up to 10 carbon atoms inclusive and carbon-carbon unsaturation at least adjacent to the carbon atom bound to G, and G is halide, preferably chloride or bromide, or lower alkoxy. When an ether derivative of the hydroxyaryl-substituted spirodilactam is desired, the E moiety is preferably allyl, propargyl or styrylmethyl and is generally provided as the halide. Allyl chloride, allyl bromide, propargyl bromide and p-vinylbenzyl chloride are illustrative. When an ester derivative of the hydroxyaryl-substituted spirodilactam is desired, the preferred acrylyl or methacrylyl moiety is typically provided as the alkoxide, i.e., as the acrylic or methacrylic ester, or as the halide, i.e., the acid halide. Methyl acrylate, methyl methacrylate, ethyl methacrylate, methacrylyl chloride or acrylyl bromide are illustrative of suitable sources of the unsaturated moiety for unsaturated ester derivatives.

The reaction of the alkali metal salt of the hydroxyaryl-substituted spirodilactam and the E-G compound is conducted in liquid phase solution in the presence of a reaction diluent. Preferred diluents are polar diluents in which the compounds undergoing reaction are soluble, at least at reaction conditions. Suitable reaction diluents include N-alkylamides such as N,N-dimethylacetamide, N,N-dimethylformamide and N-methyl-2-pyrrolidone, phenols such as phenol and m-cresol and sulfur containing solvents such as sulfolane and dimethyl sulfoxide. The compound which provides the unsaturated portion of the derivatives of the invention is utilized in a molar amount equal to or in excess over the alkali metal salt. Molar ratios of reactants from about 5:1 to about 1:1 are preferred. The stoichiometry of the reaction would suggest reaction of the E-G compound and the alkali metal salt in a 2:1 ratio. Ratios from about 1.75:1 to about 2:5 are preferred.

Reaction is effected by charging the unsaturated moiety compound, the alkali metal salt of the hydroxyaryl-substituted spirodilactam and the reaction diluent to a suitable reactor and maintaining the reaction mixture under reaction conditions. Alternatively, however, the alkali metal salt is produced in situ by providing the hydroxyaryl-substituted spirodilactam to the reaction mixture and adding a sufficient amount of an alkali metal hydroxide, carbonate or bicarbonate to neutralize the spirodilactam. In this modification it is useful to add a second solvent with which the water present or formed during neutralization is removed as an azeotrope. Toluene and ethylbenzene are illustrative of suitable azeotropic distillation solvents.

Reaction to produce the unsaturated ether or ester derivatives of the hydroxyaryl-substituted spirodilactams is conducted over a range of reaction temperatures. Suitable reaction temperatures are from about −30° C. to about 200° C., preferably from about 10° C. to about 175° C. The higher portion of the temperature range is preferred for ether production while the esters are most often formed in the lower portion of the temperature range. A suitable reaction pressure is one which will serve to maintain the reaction mixture in the liquid phase. Such pressures are typically up to about 20 atmospheres, but more often are from about 0.8 atmosphere to about 5 atmospheres. Reactant contact is maintained during reaction by conventional methods such as shaking or stirring and subsequent to reaction the ether or ester derivative product is recovered by typical methods such as selective extraction, solvent removal or precipitation followed by filtration or decantation.

The ether and ester derivatives of the hydroxyaryl-substituted spirodilactams find utility as thermosetting resins which are employed in the production of cured or crosslinked products useful as surface coatings, in adhesive formulations and in fiber-reinforced composites wherein, for example, the reinforcing fiber is glass or carbon. Such products are produced by conventional methods. The cured products are also useful in the production of hollow objects as by filament winding and are employed as impregnating and casting resins.

The curing of the unsaturated ethers or esters is accomplished by conventional methods such as thermal or photochemical excitation, by catalyzed polymerization employing cationic or anionic catalysts, or by reaction with a polyfunctional curing agent. Anionic polymerization uses alkali metal alcoholates, hydroxides or amides as catalyst while typical cationic polymerization catalysts are inorganic or organic acids or are Lewis acids. Such cationic catalysts include sulfuric acid, phosphoric acid, p-toluenesulfonic acid, boron trifluoride and tin tetrachloride. Catalytic catalysts are generally employed in a quantity of from about 0.05% by weight to about 5% by weight, based on total composition. In an alternate modification, the unsaturated ethers and esters are cured by heating with a substantial amount, e.g., from about 20% by weight to about 50% by weight, based on total composition, of a polyfunctional curing agent. One class of such curing agents comprises the bis-maleimides described by Zahir et al, U.S. Pat. No. 4,100,140. Other classes of polyfunctional curing or crosslinking agents are well known in the art.

The invention is further illustrated by the following Illustrative Embodiment which should not be construed as limiting.

ILLUSTRATIVE EMBODIMENT

To a three liter three-necked flask was added a mixture of 202.8 g (0.6 mole) of 1,6-di(4-hydroxphenyl)-1,6-diazaspiro[4.4]nonane-2,7-dione, 91.22 g (0.6 mole) of potassium carbonate, 200 ml of toluene and 1 liter of N,N-dimethylacetamide. The mixture was heated to 150° C.-160° C. and water was removed by azeotropic distillation. When the water removal was complete, the temperature was lowered to 80°-90° C. and 200.2 g (1.66 mole) of allyl bromide in 200 ml of N,N-dimethylacetamide was added over the next 80 minutes. The reaction temperature was then raised for 12 hours. The resulting mixture was cooled and filtered and the concentrated solution was then poured slowly into a mixture of hexane and ether. The precipitated product was recovered by filtration and dried in a vacuum oven at 80° C. The product had a melting point of 152°-155° C. and the nuclear magnetic resonance spectra of the product were consistent with the formula 1,6-di(4-allyloxyphenyl)-1,6-diazaspiro[4.4]nonane-2,7-dione.

ILLUSTRATIVE EMBODIMENT II

The product of Illustrative Embodiment I was mixed with an equal portion by weight of bismaleimide. The resulting mixture was heated at 170° C for 2 hours, at 210° C. for 2 hours and finally at 250° C. for 6 hours. The resulting cured product was insoluble in common solvents and had a glass transition temperature of 312° C.

ILLUSTRATIVE EMBODIMENT III

To a three liter three-necked flask was added a mixture of 135.2 g (0.4 mole) of 1,6-di(4-hydroxyphenyl)-1,6-diazaspiro[4.4]nonane-2,7-dione, 58.0 (0.42 mole) of potassium carbonate, 500 ml of N,N-dimethylformamide and 200 ml of toluene. The mixture was heated to 150°-160° C. and the water formed was removed by azeotropic distillation. When the water removal was complete, the temperature was lowered to 80°-90° C. and 95.2 g (0.8 mole) of propargyl bromide in 100 ml of N,N-dimethylformamide was added over a 2.5 hour period. The reaction temperature was raised to 100° C. and maintained at that temperature for 12 hours. The resulting solution was cooled, filtered and reduced in volume upon a rotary evaporator. The concentrated solution was poured slowly into water to give a precipitated product which was recovered by filtration and dried in a vacuum oven at 80° C. The product had a melting point of 210°-216° C. and the nuclear magnetic resonance spectra were consistent with the structure 1,6-di(4-proparglyoxyphenyl)-1,6-diazaspiro[4.4]nonane-2,7-dione. This product was cured by heating for 12 hours at 210° C. The cured product had a glass transition temperature of 305° C.

What is claimed is:

1. An unsaturated ether or ester derivative of a hydroxyaryl-substituted spirodilactam, said spirodilactam having nitrogen atoms in the 1- and 6-positions of the spiro ring system and having a hydroxyaryl substituent on each spiro ring nitrogen atom, said derivatives being unsaturated moiety derivatives of the oxyaryl residue of each hydroxyaryl substituent, the unsaturated moiety of the ether or ester having up to 10 carbon atoms and carbon-carbon unsaturation at least adjacent to the carbon atom through which the unsaturated ether or ester moiety is bound to an oxyaryl residue of the hydroxyaryl substituent.

2. The derivative of claim 1 of the formula

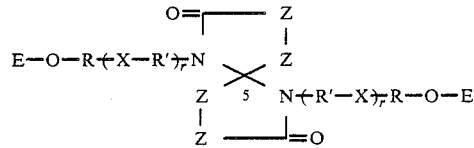

wherein Z independently is

in which Z' independently is hydrogen lower alkyl or halogen, or Z is such that two adjacent Z groups taken together form a ring system Z" of from 5 to 7 atoms, up to two of which are selected from nitrogen. Oxygen or sulfur, there being up to 15 carbon atoms in each Z", two of which form a bridge between a carbonyl carbon and the spiro carbon; R is aromatic of up to 15 carbon atoms and up to two aromatic rings, inclusive; R' is R or aliphatic of up to 10 carbon atoms inclusive; r is 0 or 1; X is a direct valence bond, alkylene of up to 8 carbon atoms inclusive, oxo, thio, sulfonyl, carbonyl, dioxyphenylene, 2,2-di(oxyphenyl) propane or dioxydiphenylene; and E independently is allyl, propargyl, 4-styrylmethyl, acrylyl or methacrylyl.

3. The derivative of claim 2 wherein each r is 0.

4. The derivative of claim 3 wherein each E is allyl, propargyl or styrylmethyl.

5. The derivative of claim 4 wherein R is phenylene.

6. The derivative of claim 4 wherein the phenylene is p-phenylene.

7. The derivative of claim 4 wherein each Z is acyclic.

8. The derivative of claim 7 of the structure 1,6-di(allyloxyphenyl)-1,6-diazaspiro[4.4]nonane-2,7-dione.

9. The derivative of claim 8 of the structure 1,6-di(4-allyloxyphenyl)-1,6-diazaspiro[4.4]nonane-2,7-dione.

10. The derivative of claim 7 of the structure 1,6-di(4-propargyloxyphenyl)-1,6-diazaspiro[4.4]nonane-2,7-dione.

11. The derivative of claim 4 wherein the adjacent Z moieties take together form Z".

12. The derivative of claim 11 of the structure 1,6-di(allyloxyphenyl)-3,4,8,9-dibenzo-1,6-diazaspiro[4.4]nonane-2,7-dione.

13. The derivative of claim 12 of the structure 1,6-di(4-allyloxyphenyl)-3,4,8,9-dibenzo-1,6-diazaspiro[4.4]nonane-2,7-dione.

14. The process of producing an unsaturated ether or ester derivative of a hydroxyaryl-substituted spirodilactam which comprises contacting, under reaction conditions in the liquid phase, (a) an unsaturated compound of the formula E-G wherein E is an unsaturated ether moiety or an unsaturated ester moiety of up to 10 carbon atoms having carbon-carbon unsaturation at least adjacent to the carbon atom bound to G, and G is halo or alkoxy, and (b) a hydroxyaryl-substituted [4.4]spirodilactam having nitrogen atoms in the 1- and 6-positions of the spiro ring system and having a hydroxyaryl substituent on each spiro ring nitrogen.

15. The process of claim 14 wherein the hydroxyaryl-substituted spirodilactam is represented by the formula

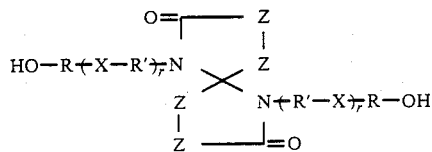

wherein Z is independently is $$\diagdown_{C(Z')_2}\diagup$$

in which Z' independently is hydrogen, lower alkyl or halogen, or Z is such that two adjacent Z groups taken together form a ring system Z" of from 5 to 7 carbon atoms, up to two of which are selected from nitrogen, oxygen and sulfur, there being up to 15 carbon atoms in each Z", two of which form a bridge between a carbonyl carbon and the central spiro carbon; R is aromatic of up to 15 carbon atoms and up to 2 aromatic rings, inclusive; R' is R or aliphatic of up to 10 carbon atoms inclusive; r is 0 or 1; and X is a direct valence bond, alkylene of up to 8 carbon atoms inclusive, oxo, thio, sulfonyl, carbonyl, dioxyphenylene, 2,2-di(oxyphenyl)propane or dioxydiphenylene.

16. The process of claim 15 wherein E is allyl, propargyl or styrylmethyl.

17. The process of claim 16 wherein each Z is acyclic.

18. The process of claim 17 wherein the spirodilactam is 1,6-di(hydroxyphenyl)-1,6-diazaspiro[4.4]nonane-2,7-dione.

19. The process of claim 18 wherein the spirodilactam is 1,6-di(4-hydroxyphenyl)-1,6-diazaspiro[4.4]nonane-2,7-dione.

20. The process of claim 19 wherein E-G is allyl chloride.

21. The process of claim 19 wherein E-G is propargyl bromide.

22. The process of claim 16 wherein adjacent Z moieties taken together form Z".

23. The process of claim 22 wherein the spirodilactam is 1,6-di(4-hydroxyphenyl)-3,4,8,9-dibenzo-1,6-diazaspiro[4.4]nonane-2,7-dione.

24. The process of claim 23 wherein E-G is allyl chloride.

* * * * *